US010813204B2

(12) United States Patent
Ernest et al.

(10) Patent No.: US 10,813,204 B2
(45) Date of Patent: Oct. 20, 2020

(54) SYSTEM AND METHOD FOR GRID CONTROL OF AN ELECTROMAGNETIC RAY TUBE

(71) Applicant: GENERAL ELECTRIC COMPANY, Schenectady, NY (US)

(72) Inventors: Philippe Ernest, Buc (FR); Stephane Gautrais, Buc (FR); Etienne Clemot, Buc (FR); Nicolas Levilly, Buc (FR); Dominique Poincloux, Buc (FR); Antonio Caiafa, Schenectady, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 249 days.

(21) Appl. No.: 16/112,053

(22) Filed: Aug. 24, 2018

(65) Prior Publication Data

US 2020/0068692 A1 Feb. 27, 2020

(51) Int. Cl.
*H01J 21/00* (2006.01)
*H05G 1/08* (2006.01)
*A61B 6/00* (2006.01)

(52) U.S. Cl.
CPC .............. *H05G 1/085* (2013.01); *A61B 6/504* (2013.01)

(58) Field of Classification Search
CPC .......... H05G 1/085; H05G 1/46; A61B 6/504; A61B 6/56; H02M 7/53871; H01R 13/53; H01F 30/02
See application file for complete search history.

(56) References Cited

U.S. PATENT DOCUMENTS

| 4,209,406 | A | 6/1980 | Goetzl | |
| 4,532,644 | A * | 7/1985 | Yamaguchi | ............ A61B 6/032 378/106 |
| 6,418,191 | B1 | 7/2002 | Fehre | |
| 6,452,102 | B1 | 9/2002 | DeForest, Jr. et al. | |
| 7,741,945 | B2 | 6/2010 | Godbey | |
| 10,014,623 | B2 | 7/2018 | Ernest et al. | |
| 2009/0036939 | A1 | 2/2009 | Singh et al. | |
| 2015/0213994 | A1 | 7/2015 | Berk et al. | |

OTHER PUBLICATIONS

European patent application 19193159.1 filed Aug. 22, 2019; European Search Report dated Jan. 21, 2020; 8 pages.

* cited by examiner

*Primary Examiner* — David P Porta
*Assistant Examiner* — Mamadou Faye
(74) *Attorney, Agent, or Firm* — Grogan, Tuccillo & Vanderleeden, LLP

(57) ABSTRACT

A system for grid control of an electromagnetic ray tube is provided. The system includes a power source, a rectifier, and a grid conductor. The power source is disposed apart from the electromagnetic ray tube and operative to generate an AC current. The rectifier is integrated into the electromagnetic ray tube and electrically coupled to a grid electrode of the electromagnetic ray tube. The grid conductor electrically couples the power source to the rectifier. The rectifier is operative to convert the AC current to a DC current that powers the grid electrode.

20 Claims, 11 Drawing Sheets

SYSTEM AND METHOD FOR GRID CONTROL OF AN ELECTROMAGNETIC RAY TUBE

BACKGROUND

Technical Field

Embodiments of the invention relate generally to medical imaging systems, and more specifically, to a system and method for grid control of an electromagnetic ray tube.

Discussion of Art

Many imaging systems utilize X-ray tubes to generate images of an object. X-ray tubes generally include a cathode with electron emitter disposed at a distance from an anode within a vacuum vessel. The anode usually includes an impact zone that is generally fabricated from a refractory metal with a high atomic number, such as tungsten or tungsten alloy. A voltage difference is maintained between the cathode and the anode such that an electron beam, also referred to herein as the "tube current", is generated by the electron emitter and strikes the anode within the impact zone, typically called the focal spot. As electrons within the electron beam impact the anode, their kinetic energy is converted to high-energy electromagnetic radiation, e.g., X-rays. Many such X-ray tubes may be monopolar, e.g., having an anode at ground potential and a cathode at a negative potential, or bipolar, e.g., having an anode at a positive potential and a cathode at a negative potential.

In many X-ray systems, the flow of the tube current between the anode and the cathode is controlled by a device known as a grid electrode that regulates the flow of the tube current between the cathode and the anode by introducing/removing a voltage between the cathode and the anode. For example, many grid electrodes are disposed in X-ray tubes so as to cutoff/restrict the tube current from flowing between the cathode to the anode by introducing a voltage, referred to herein as the "grid voltage", that repels electrons away from the anode. As will be understood, grid voltages are typically negative, e.g., negative five kilovolts (−5 kV) with respect to a cathode voltage of about negative one-hundred-and-twenty kilo volts (−120 kV). Thus, removing a grid voltage, e.g., making the grid electrode neutral, allows the tube current to flow from the cathode to the anode.

Traditional grid electrodes are typically powered by a DC current generated by a power source too large to be disposed within and/or on the X-ray tube. Thus, in many X-ray systems, the DC current is carried from the power source to the grid electrode via a conductor, referred to herein as the "grid conductor", contained within a cable, referred to herein as the "high voltage cable" and/or "HV cable", that often also carries another conductor, referred to herein as the "filament conductor" to the cathode. As will be understood, many such filament conductors carry high voltages, e.g., about one-hundred-and-twenty kilovolts (120 kV).

As will be appreciated, however, having the grid conductor with DC current and the filament conductor in the same high voltage cable generates a capacitance between the grid conductor and the filament conductor, which in turn, limits the speed at which tube current can be cycled on and off.

What is needed, therefore, is an improved system and method for grid control of an electromagnetic ray tube.

BRIEF DESCRIPTION

In an embodiment, a system for grid control of an electromagnetic ray tube is provided. The system includes a power source, a rectifier, and a grid conductor. The power source is disposed apart from the electromagnetic ray tube and operative to generate an AC current. The rectifier is integrated into the electromagnetic ray tube and electrically coupled to a grid electrode of the electromagnetic ray tube. The grid conductor electrically couples the power source to the rectifier. The rectifier is operative to convert the AC current to a DC current that powers the grid electrode.

In another embodiment, a method for grid control of an electromagnetic ray tube is provided. The method includes generating an AC current via a power source disposed apart from the electromagnetic ray tube, and conducting the AC current to a rectifier via a grid conductor, the rectifier being integrated into the electromagnetic ray tube. The method further includes converting the AC current to a DC current via the rectifier, and powering a grid electrode of the electromagnetic ray tube via the DC current.

In yet another embodiment, a non-transitory computer readable medium storing instructions is provided. The stored instructions adapt a controller to generate an AC current via a power source disposed apart from an electromagnetic ray tube; and to rectify the AC current to a DC current via a rectifier integrated into the electromagnetic ray tube, the rectifier electrically coupled to the power source via a grid conductor. The stored instructions further adapt the controller to power a grid electrode of the electromagnetic ray tube via the DC current.

DRAWINGS

The present invention will be better understood from reading the following description of non-limiting embodiments, with reference to the attached drawings, wherein below:

Figure 1:
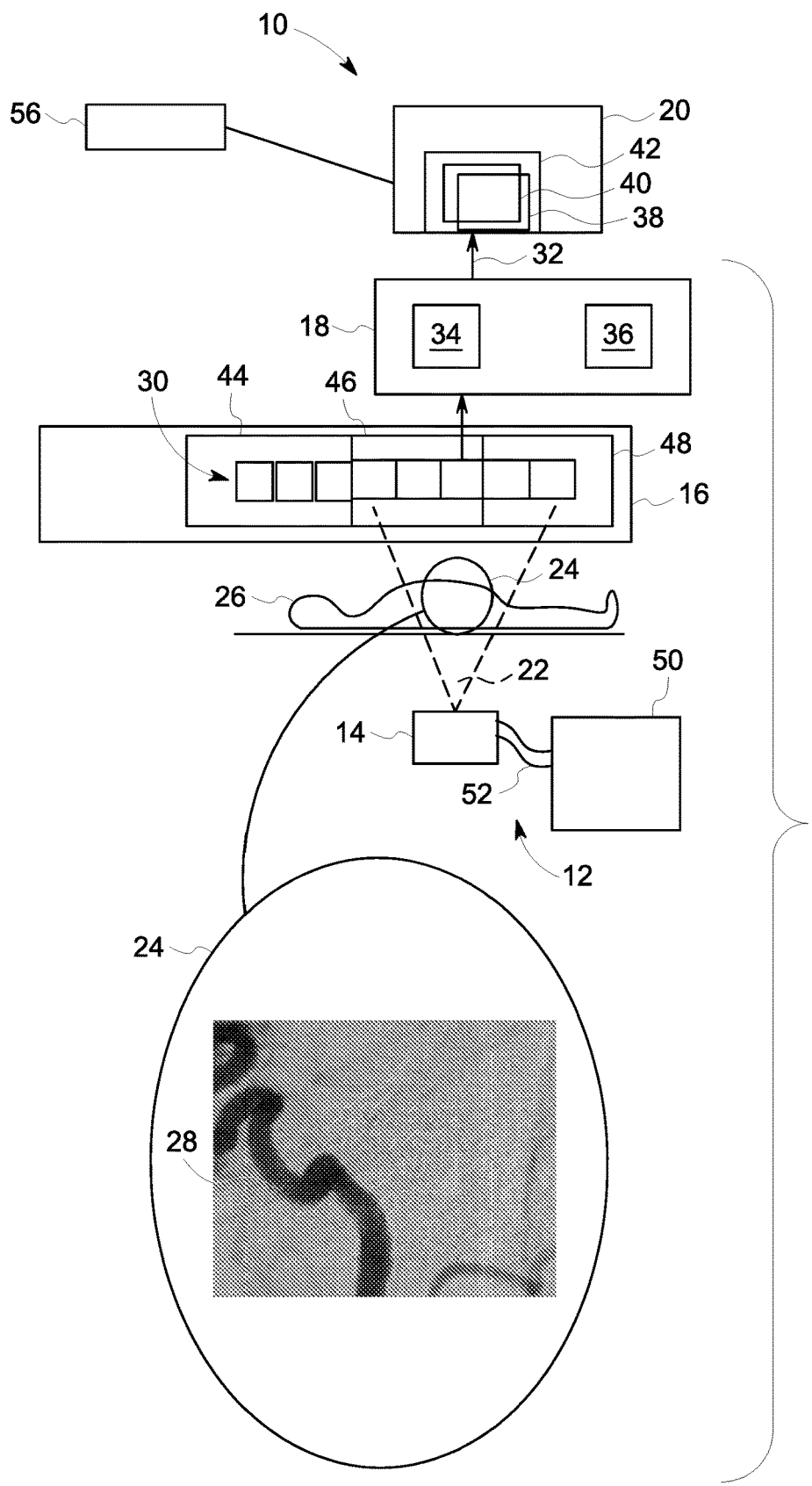
FIG. 1 is a schematic diagram of an imaging system that includes a system for grid control of an electromagnetic ray tube, in accordance with an embodiment of the present invention.
Figure 2:
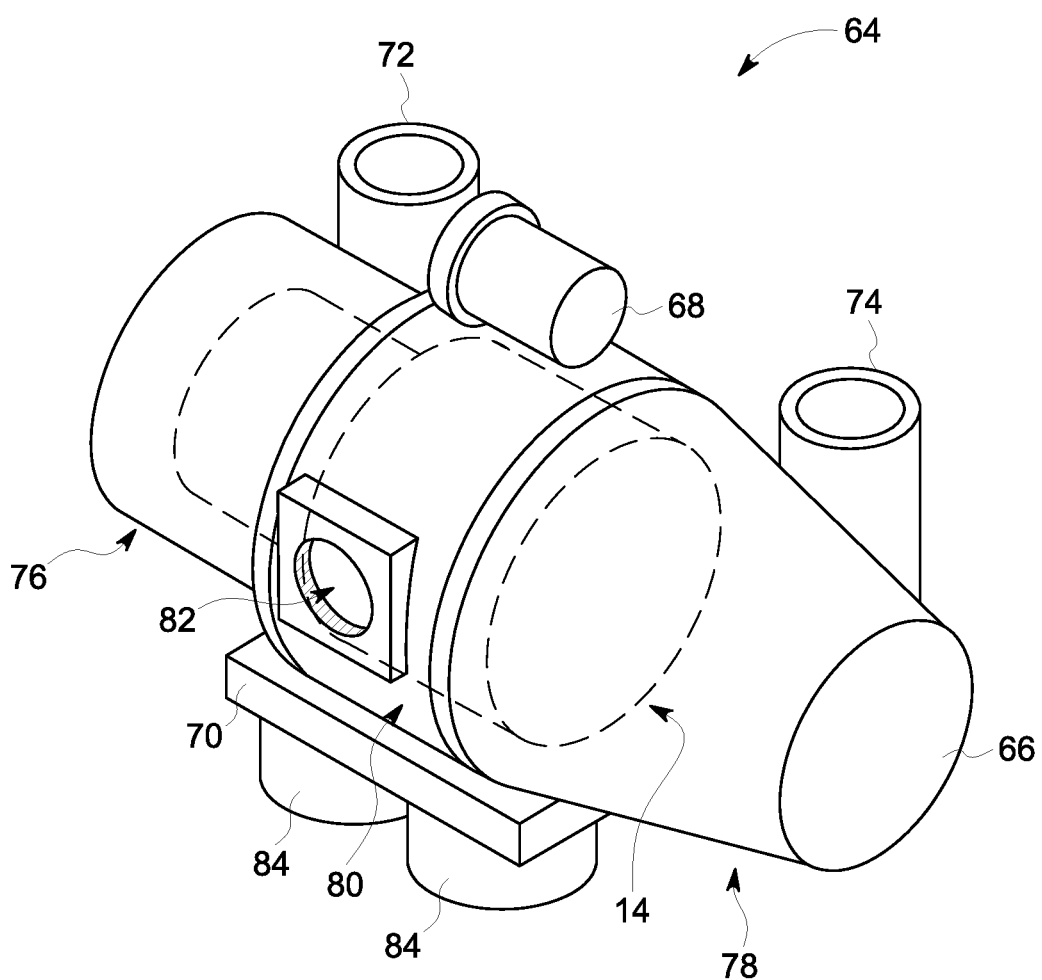
FIG. 2 is a diagram of a housing unit for an electromagnetic ray tube of the imaging system of FIG. 1, in accordance with an embodiment of the present invention.
Figure 3:
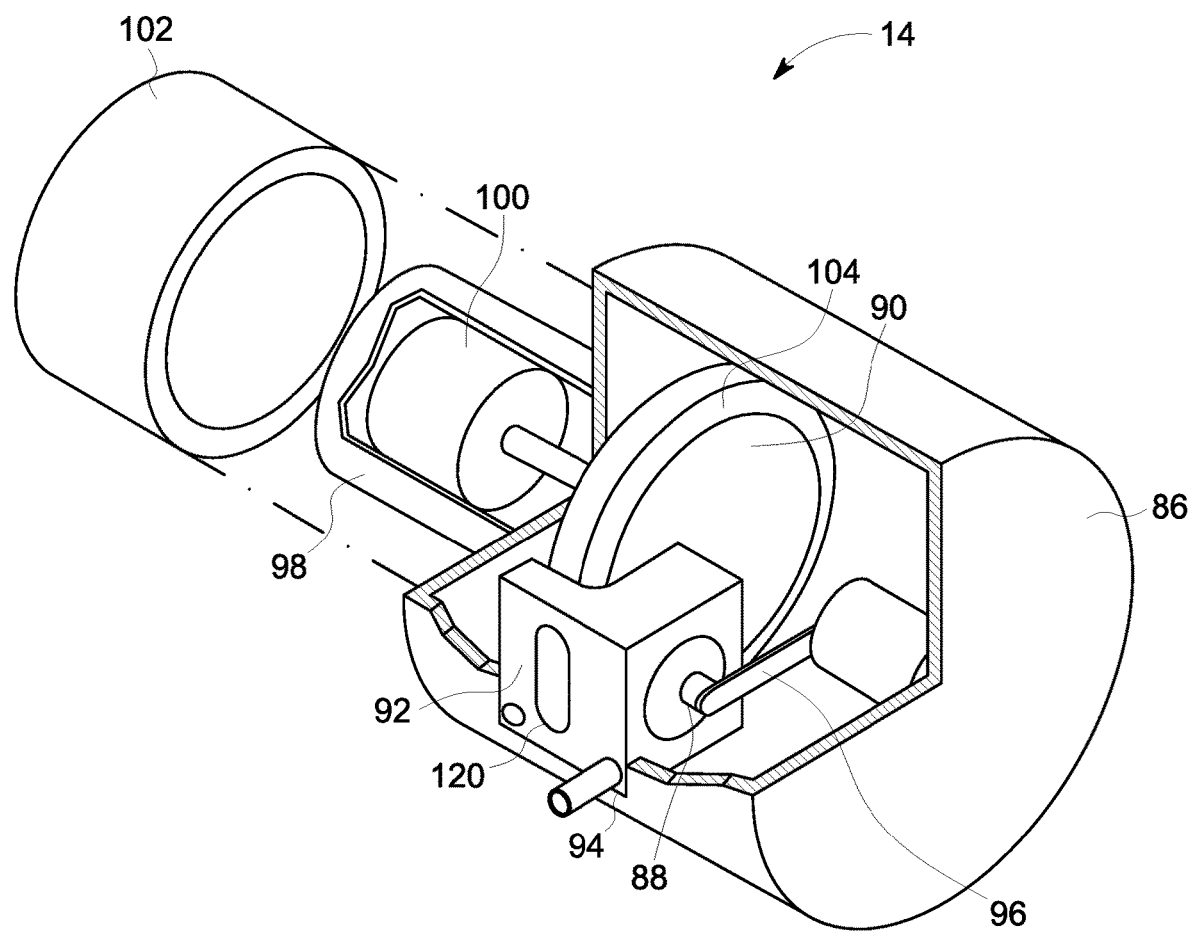
Figure 4:
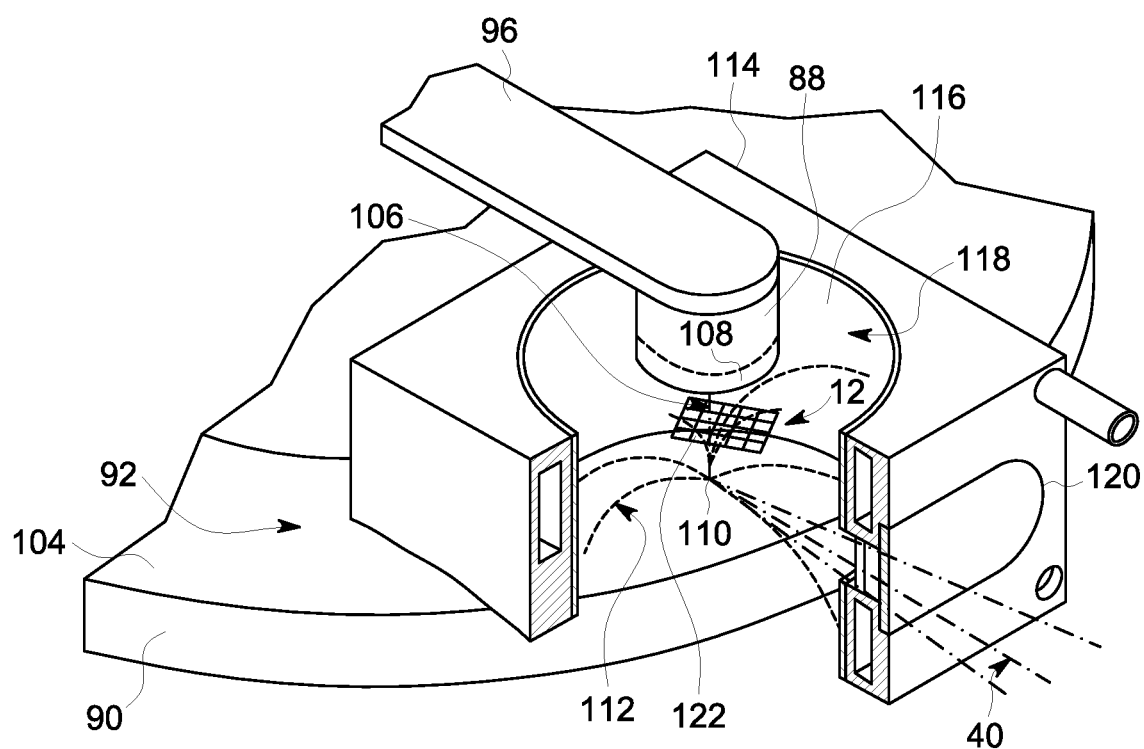
Figure 5:
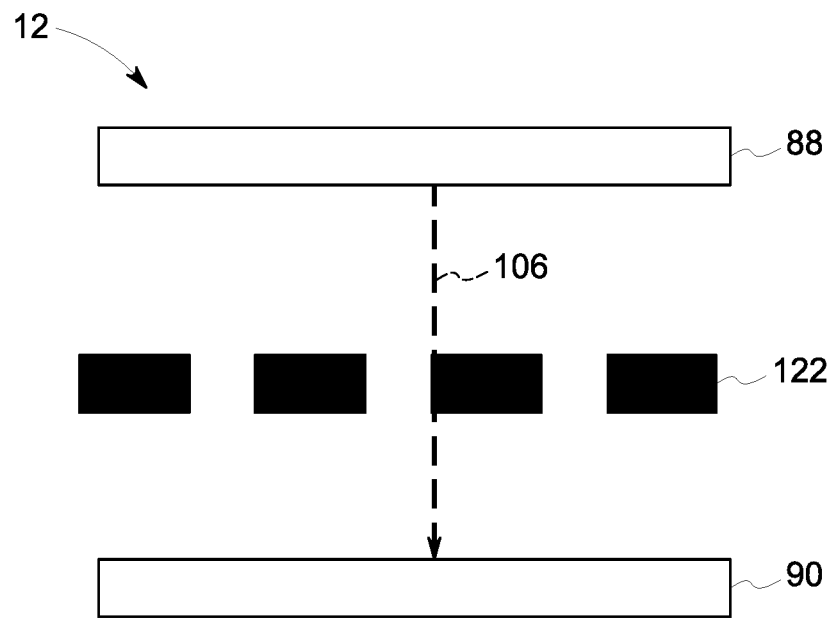
Figure 6:
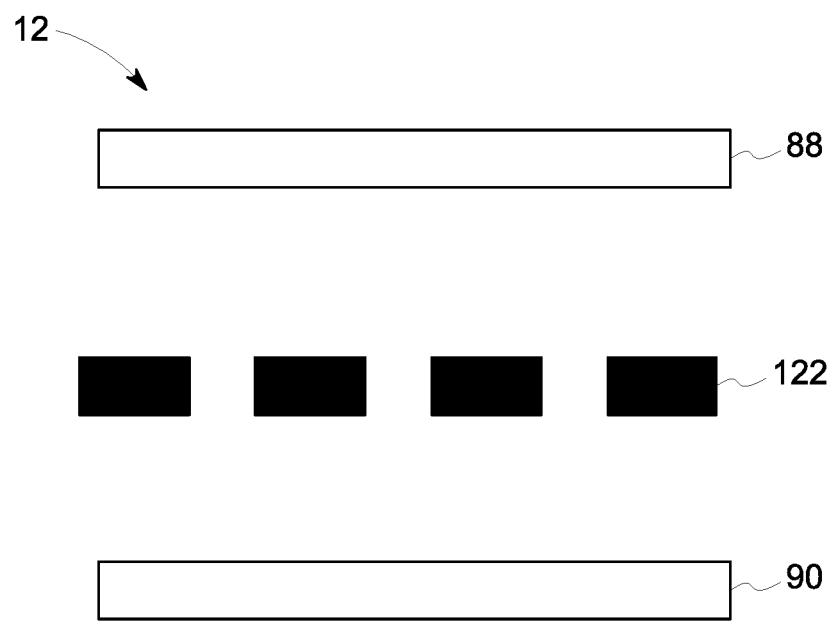
Figure 7:
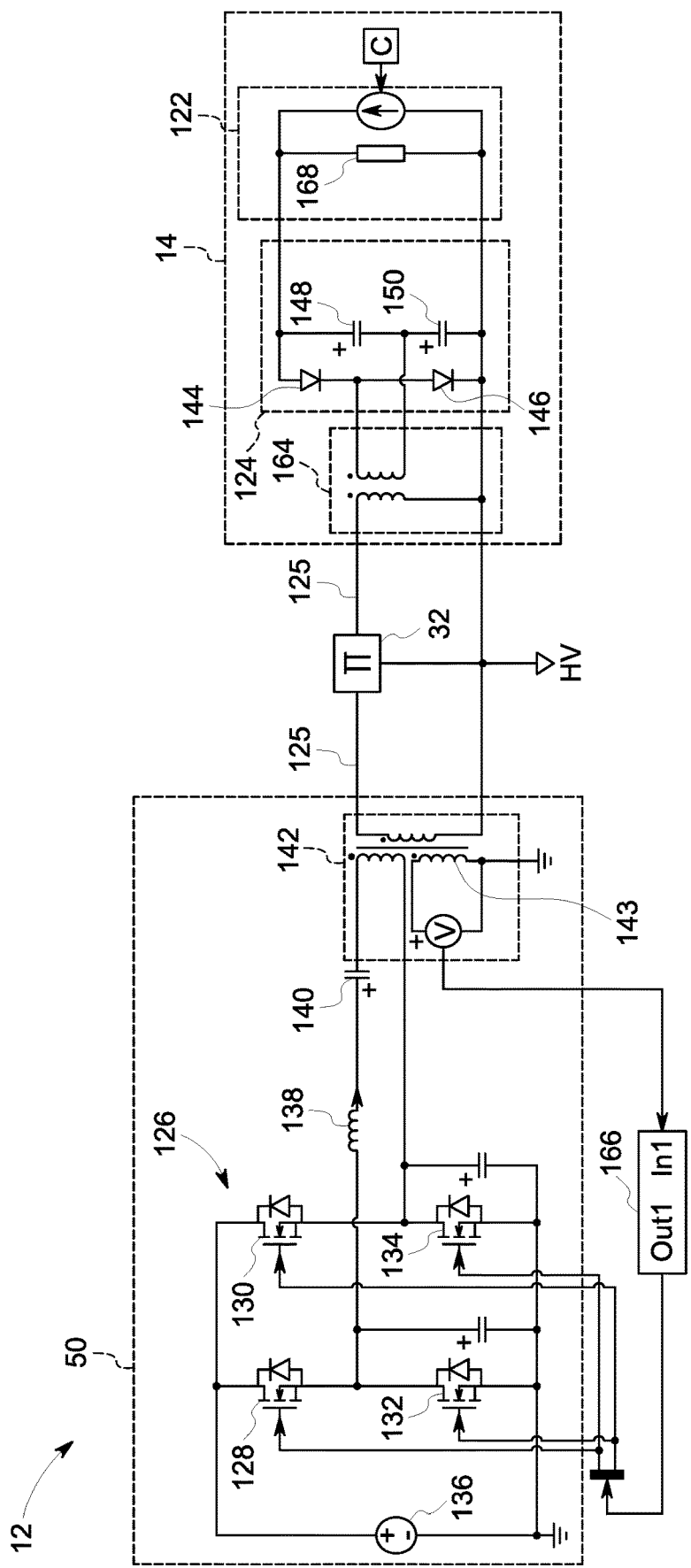
Figure 8:
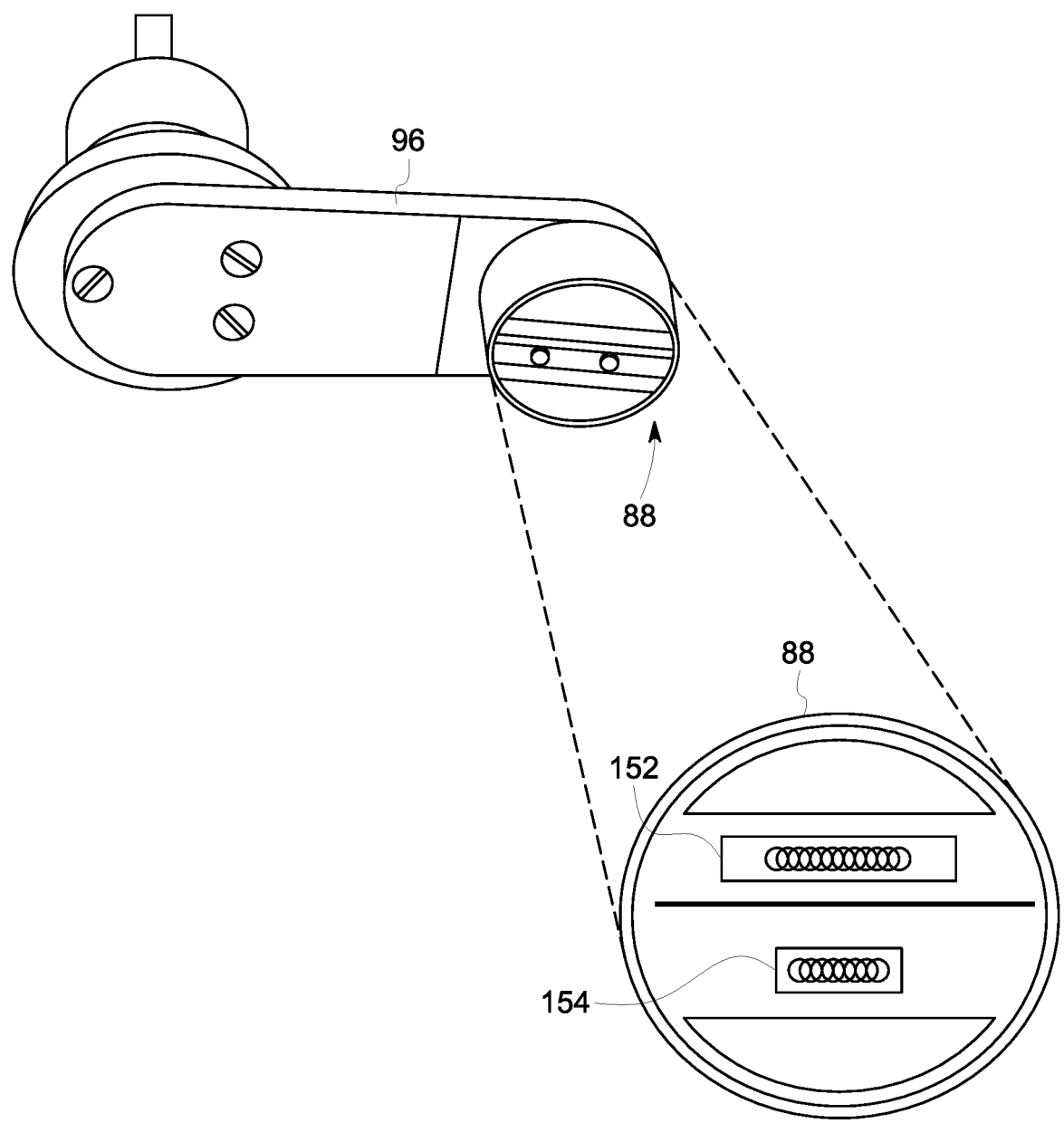
Figure 9:
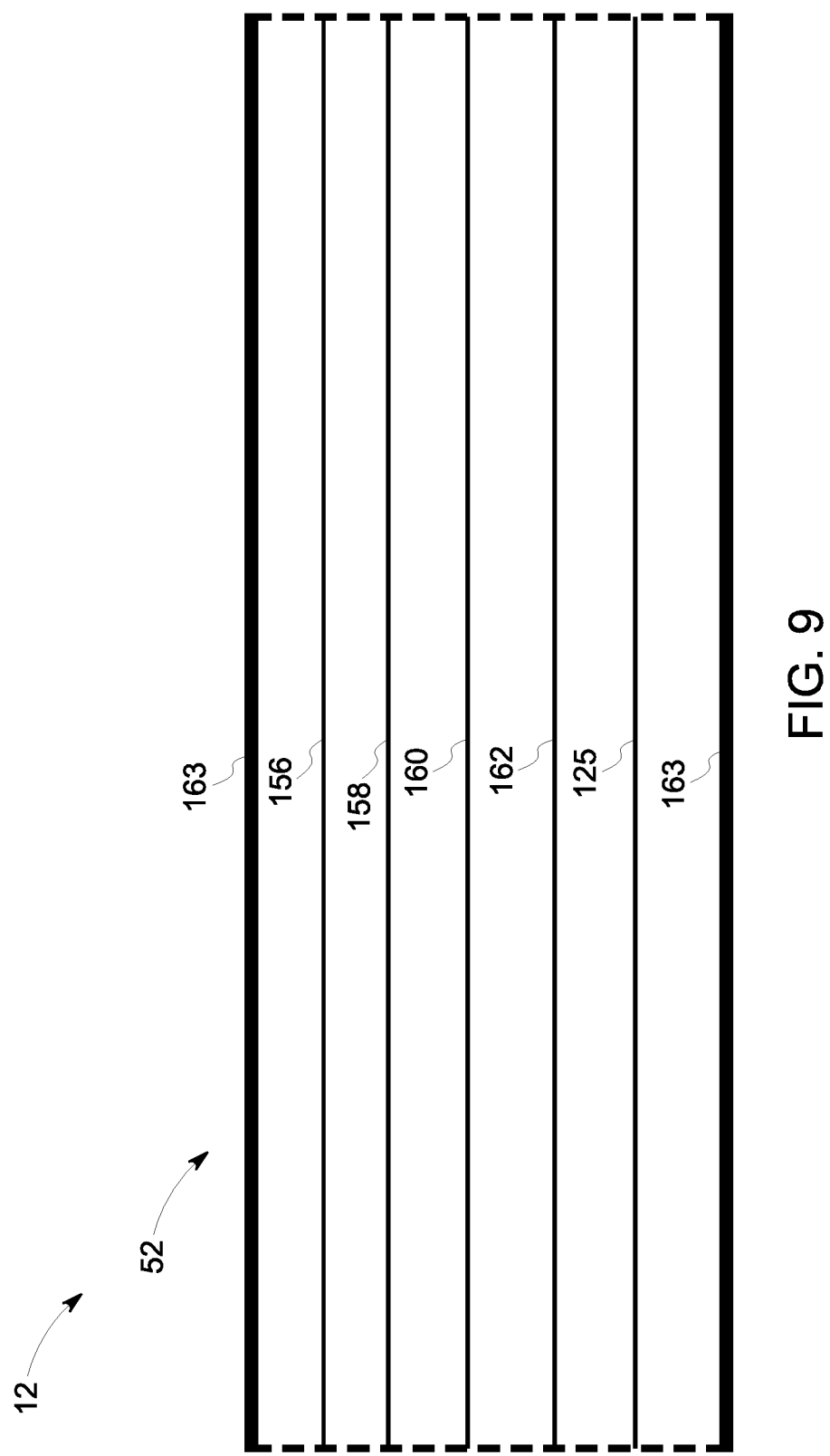
Figure 10:
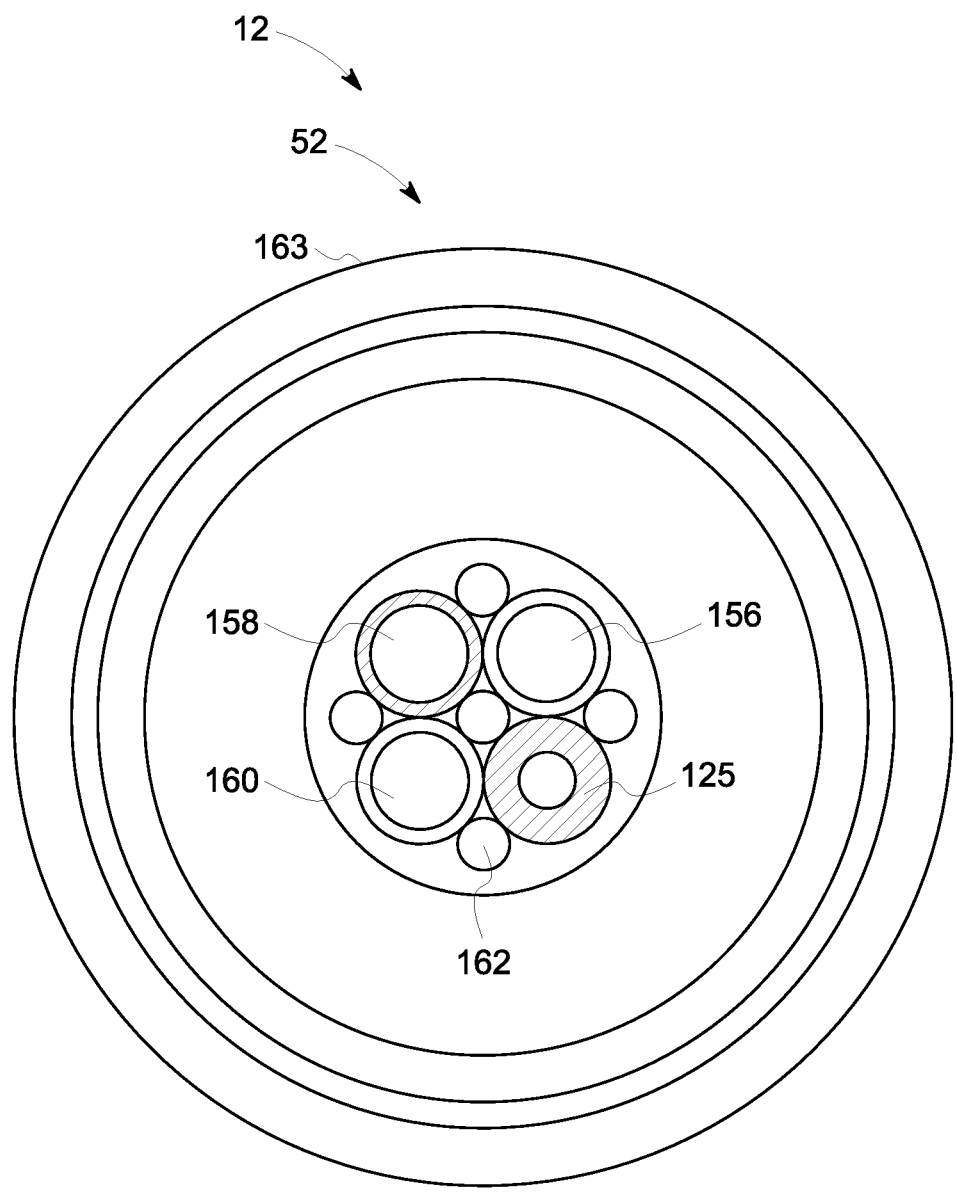
Figure 11:
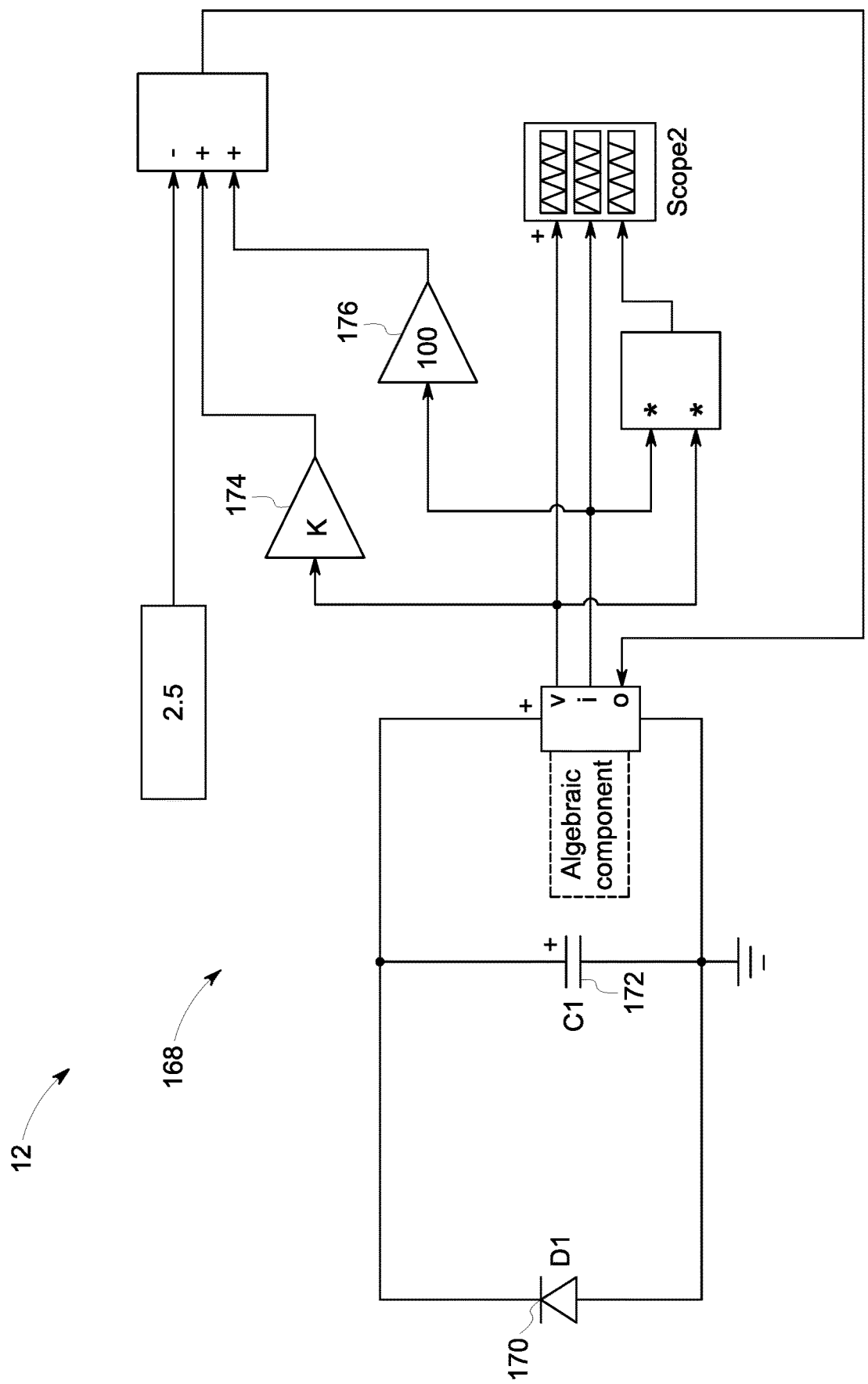
Figure 12:
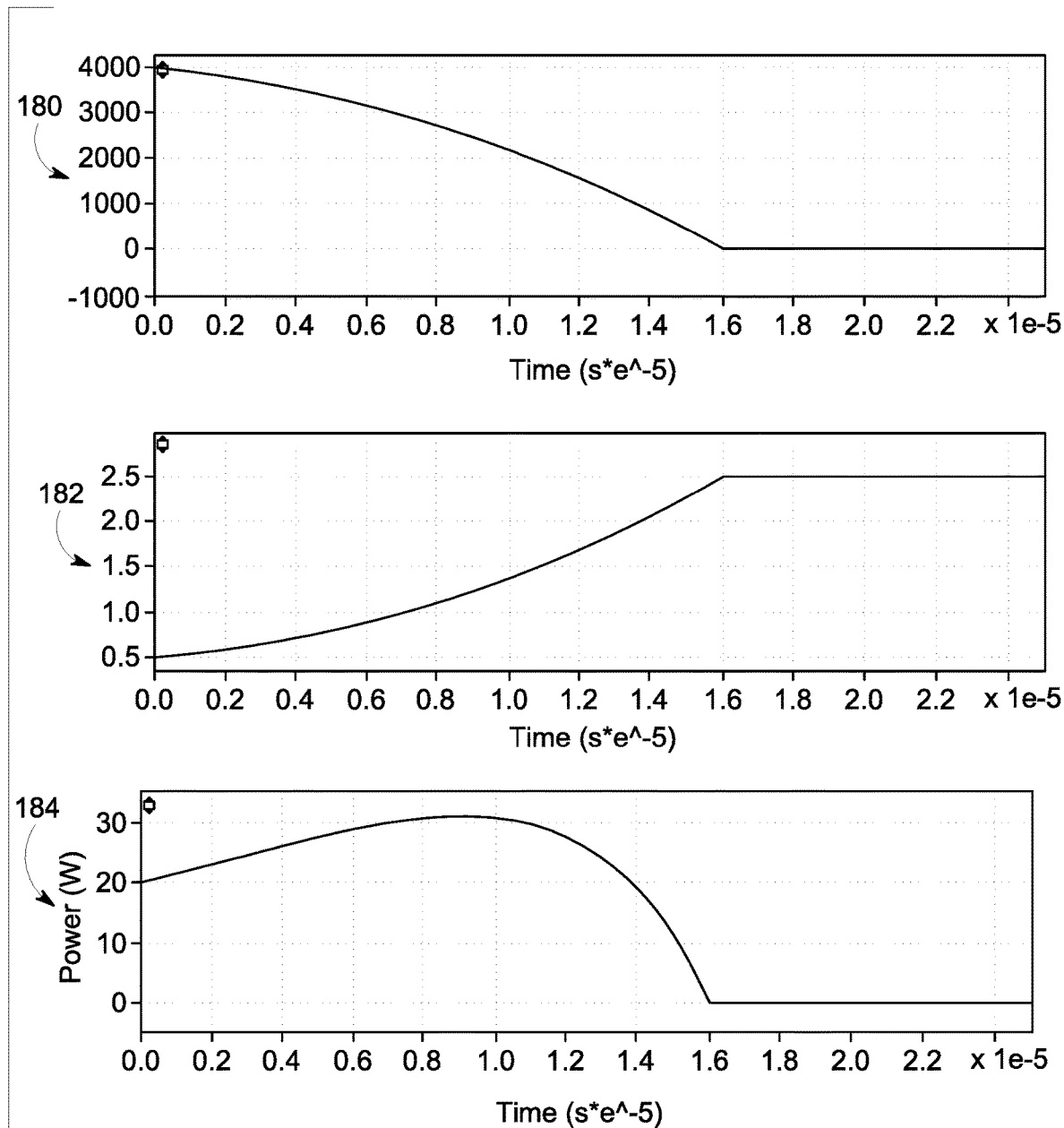

FIG. 3 is a perspective view of the electromagnetic ray tube of the imaging system of FIG. 1, wherein a motor of the electromagnetic ray tube has been exploded to reveal a stator, and wherein a portion of a vacuum vessel of the electromagnetic ray tube and a portion of the stator have been cutaway to reveal an anode of the electromagnetic ray tube mounted to a rotor of the motor, in accordance with an embodiment of the present invention;

FIG. 4 is a close up perspective view of an electron collector disposed within the electromagnetic ray tube of FIG. 3, wherein a portion of the electron collector has been cutaway to reveal a focal point of an electron beam on the anode, in accordance with an embodiment of the present invention;

FIG. 5 is a block diagram of a grid electrode disposed between an anode and a cathode of the electromagnetic ray tube of FIG. 2, wherein the grid electrode is not excited, in accordance with an embodiment of the present invention;

FIG. 6 is another block diagram of the grid electrode of FIG. 5, wherein the grid electrode is excited, in accordance with an embodiment of the present invention;

FIG. 7 is an electrical schematic of the system for grid control of an electromagnetic ray tube of FIG. 1, in accordance with an embodiment of the present invention;

FIG. 8 is a diagram of the cathode of the electromagnetic ray tube of FIG. 2, in accordance with an embodiment of the present invention;

FIG. 9 is a side-view diagram of a high voltage cable of the imaging system of FIG. 1, having one or more conductors disposed therein, in accordance with an embodiment of the present invention;

FIG. 10 is cross-sectional view of the high voltage cable of FIG. 9, in accordance with an embodiment of the present invention;

FIG. 11 is an electrical schematic of a discharge circuit of the system for grid control of an electromagnetic ray tube of FIG. 1, in accordance with an embodiment of the present invention; and FIG. 12 is a graphical representation of the voltage, current, and power of the discharge circuit, in accordance with an embodiment of the present invention.

DETAILED DESCRIPTION

Reference will be made below in detail to exemplary embodiments of the invention, examples of which are illustrated in the accompanying drawings. Wherever possible, the same reference characters used throughout the drawings refer to the same or like parts, without duplicative description.

As used herein, the terms "substantially," "generally," and "about" indicate conditions within reasonably achievable manufacturing and assembly tolerances, relative to ideal desired conditions suitable for achieving the functional purpose of a component or assembly. As used herein, "electrically coupled," "electrically connected," and "electrical communication" mean that the referenced elements are directly or indirectly connected such that an electrical current may flow from one to the other. The connection may include a direct conductive connection, i.e., without an intervening capacitive, inductive or active element, an inductive connection, a capacitive connection, and/or any other suitable electrical connection. Intervening components may be present. The term "real-time," as used herein, means a level of processing responsiveness that a user senses as sufficiently immediate or that enables the processor to keep up with an external process. As further used herein, the terms "imaging procedure" and/or "medical imaging procedure" refer to a medical procedure that involves an imaging system to assist in accomplishing one or more tasks such as, by way of non-limiting examples, deploying/installing a stent into a blood vessel, locating an ulcer, imaging a clogged artery, suturing a patient, and/or other medical processes. The term "vacuum," as used herein, means a pressure of about zero (0) psi.

As will be explained in greater detail below, embodiments of the present invention provide for a system and method for grid control of an electromagnetic ray tube, e.g., an X-ray tube, that controls operation of an electron beam within the tube via a grid electrode powered by a DC current. Unlike traditional grid-controlled X-ray tubes that pass DC current over a grid conductor from a power source to the grid electrode, however, embodiments of the present invention pass AC current over the grid conductor and convert the AC current to DC current via a rectifier integrated into the tube itself. As the grid conductor may be disposed within a cable, e.g., an HV cable, that additionally contains one or more filament conductors carrying DC current, transferring electrical power from the power source over the cable as an AC current, as opposed to DC current, reduces and/or eliminates capacitance between the grid conductor and the filament conductors, which in turn, improves the speed at which the tube current can be cycled on and/off.

While the embodiments disclosed herein are described with respect to an X-ray based imaging system, e.g., computed tomography ("CT"), fluoroscopy, vascular, mammography, etc., it is to be understood that embodiments of the present invention are equally applicable to other devices and/or imaging systems which generate electromagnetic waves/radiation via striking an anode with an electron beam. Further, embodiments of the present invention related imaging systems may be used to analyze objects within any material which can be internally imaged, generally. As such, embodiments of the present invention are not limited to analyzing objects within human tissue.

Accordingly, referring now to FIG. 1, the major components of an imaging system 10 that includes a system 12 (also shown in FIGS. 5-7 and 9-11) for grid control of an electromagnetic ray tube/generator 14 (best seen in FIGS. 2-4), in accordance with an embodiment of the present invention, are shown. As shown in FIG. 1, the imaging system 10 includes the electromagnetic ray tube 14, a detector 16, a controller 18; and a display screen 20. The electromagnetic ray tube 14 projects a radiation beam 22 through an region of interest ("ROI") 24 of a patient/subject 26 within which a structure 28, e.g., a blood vessel, is disposed. The radiation beam 22 is received by the detector 16, which generates one or more images 30 that are then communicated to the controller 18, which generates a video feed 32 that is transmitted to and displayed by the display screen 20.

As further shown in FIG. 1, the controller 18 includes at least one processor/CPU 34 and at least one memory device 36 and is in electronic communication with the electromagnetic ray tube 14, detector 16, and/or the display screen 20. An imaging program/application may be stored in the at least one memory device 36 that, when loaded into the at least one processor 34, adapts the controller 18 to generate the video feed 32 by processing the images 30 received from the detector 16. In embodiments, the imaging program may further adapt the controller 18 to control the detector 16 and/or the electromagnetic ray tube 14.

The video feed 32 includes a plurality of frames 38, 40, and 42. As used herein, the term frame describes a composite image that may be based at least in part on one or more of the plurality of images 30 acquired by the system 10. For instance, in embodiments, a single composite image/frame 42 may be generated by registering one or more of the acquired images 30 to a reference image selected from the plurality of images 30. The registration of one or more images 30 to a reference image may increase the contrast of the structure 28 within the produced/generated frame 42. Accordingly, in embodiments, each frame 38, 40, and 42 may be based at least in part on one or more of the images 30 received by the controller 18 from the detector 16. Once a frame 42 has been generated, it is transmitted, as part of the video feed 32, by the controller 18 to the display screen 20. In other words, in embodiments, the displayed video feed 32 is a processed form of the raw images 30 acquired by the system 10. In embodiments, the video feed 32 may be a live/real-time and/or near-real-time feed. In other embodiments, one or more of the frames 38, 40, and 42 may be still images, e.g., a photograph. As will be understood, the system 10 may acquire the images 30 as part of an image acquisition 44, 46, 48, wherein the images 30 within the same acquisition 44, 46, 48 are acquired between injections of the contrast agent into the patient 26.

As also shown in FIG. 1, a power source 50 is disposed apart from the electromagnetic ray tube 14, i.e., the power source 50 is a separate device that is not integrated into the tube 14. For example, in embodiments, the power source 50 may be disposed at a distance of about twenty meters (20 m) or more away from the electromagnetic ray tube 14. Accordingly, the power source 50 is electrically coupled to the electromagnetic ray tube 14 via a grid conductor which may be disposed within a cable 52, e.g., an HV cable.

Further, in embodiments, the display/monitor 20 may be incorporated into a human machine interface ("HMI") 56 that includes a console, e.g., buttons, dials, a touch screen, a keyboard, and/or a mouse, for receiving command/scanning parameters from an operator of the systems 10 and/or 12.

Turning now to FIG. 2, the ray tube 14 may be disposed within a housing unit 64 which may include a container 66, a pump 68, a radiator 70, an anode receptacle 72, and/or a cathode receptacle 74.

The container 66 may be formed from lead and have an anode end 76, a cathode end 78, and a center section 80 disposed therebetween with an aperture/window 82. The ray generator 14 may be contained within the container 66 such that the generated rays 22 (FIG. 1) are able to pass through the aperture 82. The container 66 may be filled with air or a fluid, e.g., dielectric oil/transformer oil which, as will be discussed in greater detail below, is circulated throughout the container 66 via the pump 68 so as to cool/transfer heat away from the ray generator 14.

The radiator 70 may be disposed to one side of the center section 80 and fluidly connected to the interior of the container 66 such that the radiator 70 is able to cool the fluid by absorbing and radiating heat from it into the surrounding atmosphere. As shown in FIG. 3, in embodiments, the radiator 70 may include one or more fans 84 for providing a cooling air flow over the radiator 70 as the fluid circulates through it.

The anode 72 and cathode 74 receptacles serve as conduits through which electrical connections may be made to the ray generator 14 within the container 66.

Moving to FIG. 3, the ray generator 14 includes a vacuum enclosure/vessel 86 within which a vacuum and/or a near vacuum is maintained. The ray generator 14 further includes a cathode 88, an anode 90, and an electron collector 92, all of which are disposed within the vacuum vessel 86. The vacuum vessel 86 further includes an aperture 94 that aligns with the aperture 82 (FIG. 2) of the container 66 (FIG. 2). In embodiments, the electron collector 92 may partially protrude from the vacuum vessel 86 such that the vacuum within the vessel 86 is maintained. The cathode 88 may be mounted to the vacuum vessel 86 via an arm 96 and positioned such that it faces the anode 90. The anode 90 may be configured to rotate in relation to the cathode 88. For example, in embodiments, the ray generator 14 may further include a motor formed by a stator 98 fastened to the vacuum vessel 86 and a rotor 100 mounted to the anode 90. As will be appreciated, the motor may be electric, pneumatic, or hydraulic, and/or disposed within a casing 102 that may be mounted to the vacuum vessel 86. The anode 90 may be a circular disk with a target track 104, e.g., a tungsten ring, disposed along the circumference of the anode 90 which aligns with the cathode 88. As will be appreciated, while the figures provided herein depict the ray generator 14 as including the vacuum vessel 86, it will be understood that, in other embodiments, the ray generator 14 may not include the vacuum vessel 86.

Turning to FIG. 4, in operation, a voltage is maintained between the cathode 88 and the anode 90 such that an electron beam 106, i.e., a continuous stream of individual electrons (also shown in FIG. 5), is generated/produced by/at an filament/emitter 108 (best seen as elements 152 and/or 154 in FIG. 8) of the cathode 88 and strikes the anode 90 at a focal point 110 that falls within the target track 104. Upon striking the anode 90, the kinetic energy of some of the electrons within the electron beam 106 is converted into electromagnetic waves, i.e., the X-rays 22, which radiate out in all directions from the focal point 110. The focal point 110 and/or anode 90, however, may be located within the vacuum vessel 86 (FIG. 3) so as to increase the likelihood that individual X-rays 22 generated by the electrons striking the focal point 110 will pass through the apertures 82 (FIG. 2) and 94 (FIG. 3). As will be appreciated, the striking of anode 90 by the electron beam 106 generates heat within the portion of the anode 90 occupying the focal point 110. Accordingly, in embodiments, the anode 90 may be rotated by the rotor 100 so that the point of the target track 104 aligning with the focal point 110 shifts over time to provide points of the target track 104 an opportunity to cool in-between cycles of being struck by the election beam 106.

As will be understood, some of the electrons 112 within the beam 106 backscatter away from the focal point 110 after striking the anode 90. In particular, some of the backscattered electrons 112 will be additionally deflected about ninety degrees (90°) or more by the negative electric charge of the electron beam 106 and/or cathode 88, and thus follow a curved path that re-strikes the anode 90 at a point other than the focal point 110, which, without the electron collector 92, would generate off-focal electromagnetic rays and/or additional/unwanted heat within the anode 90.

Accordingly, the electron collector 92 has a body 114 that includes/defines a surface/interface 116 configured to intercept the backscattered electrons 112 so as to prevent them from re-striking the anode 90. For example, as shown in FIG. 4, the surface 116 may have a shape, e.g., cylindrical, spherical, rectangular, etc., that occupies space intercepting possible trajectories/paths of the backscattered electrons 112. In embodiments, the surface 116 defines a cavity 118 within which the electron beam 106 strikes the anode 90. As will be understood, backscattered electrons 112 that intercept/strike the surface 116 are subsequently absorbed by the body 114 such that their kinetic energy is transformed into heat.

As will be appreciated, the body 114 may also serve as a collimator with respect to the X-rays 22 emitted from the anode 90. For example, as further shown in FIG. 5, the body 114 may include an aperture 120 that aligns with apertures 82 (FIG. 2) and 94 (FIG. 3) such that X-rays 22 having a trajectory/path aligned with the apertures 82, 94, and 120 may pass through the body 114, vacuum vessel 86 (FIG. 3), and fluid container 66 (FIG. 2), while X-rays 22 having trajectory/paths not aligned with the apertures 82, 94, and 120 are restricted from passing through the body 114. In embodiments, the electron collector 92 collimates the generated X-ray 22 such that the X-rays 22 passing through the apertures 82, 94, and 120 define a beam with a sharp edge. In certain aspects, the electron collector 92 may include additional radiation shielding, e.g., lead, in the casing of an insert that surrounds the ray generator 14.

As yet further shown in FIG. 4, a grid electrode 122 is disposed between the cathode 88 and the anode 90. In embodiments, the grid electrode 122 may be disposed on, or otherwise integrated into, the cathode 88, e.g., within the cavity 118. As will be understood, the grid electrode 122 regulates the electron beam 106 by introducing/removing a grid voltage, e.g., −4 kV, between the cathode 88 and the anode 90, i.e., the grid electrode 122 generates a voltage that repels electrons attempting to leave the filament 108.

For example, as shown in FIG. 5, when the grid electrode 122 is not powered/excited/charged, e.g., electrically neutral, the lack of voltage allows the electron beam 106 to flow from the cathode 88 to the anode 90. Conversely, as shown in FIG. 6, when the grid electrode 122 is fully powered/excited/charged, the resulting grid voltage prevents flow of the electron beam 106 (FIGS. 4 and 5) from the cathode 88 to the anode 90, as represented by the absence of the dashed line 106. In embodiments, the amount/magnitude of grid voltage may be varied so as to vary the intensity of the electron beam 106, i.e., the grid electrode may be excited to a level less than full excitation so that some electrons are allowed to flow between the cathode 88 and the anode 90.

Moving to FIG. 7, an electrical schematic of the system 12 for control of the electromagnetic ray tube 14 is shown. The system 12 includes the power source 50, a rectifier 124, and the grid conductor 125. As discussed above, the power source 50 is operative to generate an AC current that is conducted to the rectifier 124 via the grid conductor 125. As will be understood, the rectifier 124, which is electrically coupled to the grid electrode 122, converts/rectifies the AC current into a DC current that powers the grid electrode 122.

The power source 50 may include a H-bridge/power inverter 126 formed by four switches 128, 130, 132, 134 and a voltage source 136. The h-bridge 126 may be fed/receive a forty-eight volt DC (48 VDC) input and operated in zero-voltage-switching ("ZVS") mode at about two-hundred kilohertz (200 kHz).

In embodiments, the power source 50 may further include an inductor 138, a capacitor 140, and/or a transformer 142. The capacitor 140 may have a capacitance of about ten microfarad (10 uF) and is operative to avoid any DC component in the transformer 142. As will be appreciated, the transformer 142 may provide the following three functions. First, the transformer 142 may provide for high voltage insulation between primaries at ground potential and a secondary at high voltage, e.g., negative sixty-two kilovolts (−62 kV), negative one-hundred-and-twenty-five kilovolts (−125 kV). Second, the transformer 142 may provide for impedance adaption: $Cr=5\ nF*m1^2$, where m1 is selected to achieve the desired reflected Cr and, thus, frequency. Third, the transformer 142 may provide a feedback winding 143, which as discussed below, may be used to improve control over the system 12.

While FIG. 7 depicts an embodiment of the present invention where the elements/electrical components on the primary side of the transformer 142 are at ground potential, so that the transformer 142 provides high voltage insulation, it will be understood that, in other embodiments, the primary side of the transformer 142 may be connected to a high voltage of the cathode 88. Accordingly, in such embodiments, the transformer 142 need not provide high voltage insulation.

As also shown in FIG. 7, the rectifier 124 is integrated into the electromagnetic ray tube 14 and may include one or more diodes 144, 146 and/or capacitors 148, 150. As will be understood, integration of the rectifier 124 into the electromagnetic ray tube 14 includes embodiments in which the rectifier 124 is disposed in a connector of the HV cable 52 on the electromagnetic ray tube 14 side of the HV cable 52.

As stated above, in embodiments, the grid conductor 125 may be disposed within, e.g., travel through, the cable 52 which may also contain one or more filament conductors each operative to provide the tube current/beam 106. For example, referring briefly to FIGS. 8-10, in embodiments, the cathode 88 may include two or more filaments 152, 154 for generating electromagnetic rays 22 of differing frequencies, where each filament 152, 154 is powered by a different filament conductor 156, 158, 160, 162. As shown in FIGS. 9 and 10, the grid conductor 125 may be disposed within the sidewall 163 of cable 52 in close proximity to the filament conductors 156, 158, 160, 162. Thus, as will be appreciated, in embodiments, excitation of the grid electrode 122 and/or the filaments 152, 154 produces a capacitance within the cable 52.

Accordingly, and returning back to FIG. 7, in embodiments, the cable 52 may serve/be the capacitor in a resonant/LC circuit of the power source 50, i.e., the resonant circuit formed by the cable 52 and inductor 138. As will be appreciated, the capacitance of the cable 52 varies as the length of the cable 52 varies. In embodiments, the cable 52 may have a length of between about five meters (5 m) to about thirty-eight meters (38 m), e.g., eighteen meters (18 m), twenty-four meters (24 m), thirty meters (30 m), thirty-six meters (36 m). In embodiments, the cable 52 may have a RC time constant of less than or equal to fifty microseconds (50 us). As will be appreciated, in embodiments where the cable 52 functions as the capacitor in the resonant/LC circuit of the power source 50, only the Q factor of the resonant/LC circuit changes. Thus, in embodiments where the size of the cable 52 is initially unknown and/or variable, for instance due to a cable upgrade and/or movement of the imaging system 10 to a new room/facility, the system 12 may be calibrated/initialized by entering the length of the cable 52 into the HMI 56 (FIG. 1). In other embodiments, the system 12 may have an initialization mode that begins upon initial power up of the system 10 in which the resonant frequency is measured, e.g., by analyzing current waveform.

In embodiments, the cable 52 may be flexible so as to provide for movement of the electromagnetic ray tube 14 about the patient 18. In embodiments, the cable 52 may have a length of about thirty meters (30 m) and a resonant frequency of about eight-hundred-and-sixty kilohertz (860 kHz), which, as will be appreciated, may be sufficient to prevent the cable 52 from being excited by the inverter 126 current waveform, which, in embodiments, may alter between a triangle and sine wave at about one-hundred-eighty kilohertz (180 kHz).

As will be appreciated, the resonant circuit formed by the cable 52 and the inductor 138 may resonant at a frequency of about one-hundred-and-thirty kilohertz (130 kHz), given by Lr=5 uH and a reflected capacitance of the cable 52 to the primary side of the transformer 142 with a ratio of about m1 such that $Cr=5\ nF*m1^2$.

As further shown in FIG. 7, in embodiments, the system 12 may further include a transformer 164 integrated into the electromagnetic ray tube 14 in-between the grid conductor 125 and the rectifier 124. As will be appreciated, in embodiments, the rectifier 124 and the transformer 164 may convert/condition an AC voltage of about a few hundred volts, e.g., (100-300 v) at about two-hundred kilohertz (200 kHz) to a DC current resulting in a grid voltage about four kilovolts (−4 kV) so as to keep the two-hundred kilohertz (200 kHz) current flowing into the HV cable 52 at an appropriate rate/amount, e.g., about five nanofarad (5 nF) for a thirty meter (30 m) long HV cable 52 at the two-hundred kilohertz (200 kHz) and one-hundred volts (100 V) produces a point-seven amp (0.7 A) current. In embodiments, the transformer 164 may be a step-up high frequency ferrite toroid (or a stacked toroid) transformer.

Additionally, the system 12 may further include a controller 166 that is operative to provide closed loop control of the power source 50. The controller 166 may receive, as input, a voltage signal sampled from the feedback coil 143 of transformer 142, and in turn, control the operation of the inverter 126 via one or more of the switches 128,130, 132, 134.

Referring now to FIG. 11, the system 12 may further include a discharge circuit 168 (also depicted symbolically as resistor and/or constant current source in FIG. 7) operative to facilitate removal of the grid voltage from the grid electrode 122 (FIGS. 4-7). As will be understood, FIG. 11 depicts a positive voltage with respect to ground, as opposed to a negative voltage with respect to a high voltage cathode potential. The discharge circuit 168 may include one or more diodes 170, capacitors 172, amplifiers/buffers 174, 176 and/or switches. The depicted algebraic component is a virtual component used in simulation software having/maintaining the relationship of $5e^{-4+v}+100i-2.5=0$, v being the voltage across the algebraic component and I the current flowing into the algebraic component. As will be understood, the physical realization/implementation of the algebraic component may include a TL431 reference voltage, or similar voltage, and/or one or more switches, e.g., a metal oxide semiconductor ("MOS") with an appropriate voltage rating.

Accordingly, in embodiments, the power source 50 may supply a constant, or near constant, current. For example, starting with an initial current I at voltage V, the discharge time of a capacitor C from V to 0.05V is 3RC, where R is a discharge resistor equal to V/I, may be divided by three (3) using a constant current I discharge circuit, and divided again by six (6) using a constant power discharge circuit P=VI. Thus, in embodiments, the discharge circuit may be active due to incorporated switches, but, as will be appreciated, may be considered passive as the switches need not require commands and/or auxiliary supplies. Accordingly, in embodiments, there may be two (2) current sources, e.g., each crossing a two kilovolt (2 kV) capacitor, such that the switches may be twenty-five-hundred volts (2,500 V) or four-thousand volts (4,000 V) commercial insulated-gate bipolar transistors ("IGBTs"). As shown in FIG. 12, which depicts three graphs 180, 182, and 184 respectively showing the voltage, current, and power in the discharge circuit 168, in such embodiments, a twenty watt (20 W) power source may provide for a discharge of a fifty picofarads (50 pF) capacitor from four kilovolts (4 kV) to zero volts (0 v) in about sixteen microseconds (16 us). As such, discharge of the grid voltage may be facilitated by stopping the inverter 126 so that no AC current flows to the rectifier 124. As will be appreciated, stoppage of the inverter 126 may trigger/activate the aforementioned discharge circuit so as to save the twenty watt (20 W) power dissipation.

Finally, it is also to be understood that the imaging system 10 and/or system 12 may include the necessary electronics, software, memory, storage, databases, firmware, logic/state machines, microprocessors, communication links, displays or other visual or audio user interfaces, printing devices, and any other input/output interfaces to perform the functions described herein and/or to achieve the results described herein, which may be accomplished in real-time. For example, as previously mentioned, the systems may include at least one processor and system memory/data storage structures, which may include random access memory (RAM) and read-only memory (ROM). The at least one processor of the system may include one or more conventional microprocessors and one or more supplementary co-processors such as math co-processors or the like. The data storage structures discussed herein may include an appropriate combination of magnetic, optical and/or semiconductor memory, and may include, for example, RAM, ROM, flash drive, an optical disc such as a compact disc and/or a hard disk or drive.

Additionally, a software application that adapts the controller to perform the methods disclosed herein may be read into a main memory of the at least one processor from a computer-readable medium. The term "computer-readable medium," as used herein, refers to any medium that provides or participates in providing instructions to the at least one processor of the systems 10 and/or 12 (or any other processor of a device described herein) for execution. Such a medium may take many forms, including but not limited to, non-volatile media and volatile media. Non-volatile media include, for example, optical, magnetic, or opto-magnetic disks, such as memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, a RAM, a PROM, an EPROM or EEPROM (electronically erasable programmable read-only memory), a FLASH-EEPROM, any other memory chip or cartridge, or any other medium from which a computer can read.

While in embodiments, the execution of sequences of instructions in the software application causes at least one processor to perform the methods/processes described herein, hard-wired circuitry may be used in place of, or in combination with, software instructions for implementation of the methods/processes of the present invention. Therefore, embodiments of the present invention are not limited to any specific combination of hardware and/or software.

It is further to be understood that the above description is intended to be illustrative, and not restrictive. For example, the above-described embodiments (and/or aspects thereof) may be used in combination with each other. Additionally, many modifications may be made to adapt a particular situation or material to the teachings of the invention without departing from its scope.

For example, in an embodiment, a system for grid control of an electromagnetic ray tube is provided. The system includes a power source, a rectifier, and a grid conductor. The power source is disposed apart from the electromagnetic ray tube and operative to generate an AC current. The rectifier is integrated into the electromagnetic ray tube and electrically coupled to a grid electrode of the electromagnetic ray tube. The grid conductor electrically couples the power source to the rectifier. The rectifier is operative to convert the AC current to a DC current that powers the grid electrode. In certain embodiments, the grid conductor is disposed within a cable that includes one or more filament conductors each operative to provide a tube current of the electromagnetic ray tube. In certain embodiments, the cable is a capacitor in a resonant circuit of the power source. In certain embodiments, the cable has a length of between about 5 m to about 38 m. In certain embodiments, the cable has a RC time constant of less than or equal to 50 us. In certain embodiments, the system further includes a transformer integrated into the electromagnetic ray tube in-between the grid conductor and the rectifier. In certain embodiments, the AC current has a frequency of between about 100 kHz to about 1,000 kHz. In certain embodiments, the system further includes a controller operative to provide closed loop control of the power source.

Other embodiments provide for a method for grid control of an electromagnetic ray tube. The method includes generating an AC current via a power source disposed apart from the electromagnetic ray tube, and conducting the AC current to a rectifier via a grid conductor, the rectifier being integrated into the electromagnetic ray tube. The method further includes converting the AC current to a DC current via the rectifier, and powering a grid electrode of the electromagnetic ray tube via the DC current. In certain embodiments, the grid conductor is disposed within a cable that includes one or more filament conductors each operative to provide a tube current of the electromagnetic ray tube. In certain embodiments, the cable is a capacitor in a resonance circuit of the power source. In certain embodiments, the cable has a length of between about 5 m to about 38 m. In certain embodiments, the method further includes pulsing the DC current to the grid electrode at greater than or equal to fifteen pulses per second. In certain embodiments, the method further includes transforming the AC current via a transformer integrated into the electromagnetic ray tube. In certain embodiments, the AC current has a frequency of between about 100 kHz to about 1,000 kHz. In certain embodiments, the method further includes controlling the power source via a closed loop controller.

Yet still other embodiments provide for a non-transitory computer readable medium storing instructions. The stored instructions adapt a controller to generate an AC current via a power source disposed apart from an electromagnetic ray tube; and to rectify the AC current to a DC current via a rectifier integrated into the electromagnetic ray tube, the rectifier electrically coupled to the power source via a grid conductor. The stored instructions further adapt the controller to power a grid electrode of the electromagnetic ray tube via the DC current. In certain embodiments, the stored instructions further adapt the controller to pulse the DC current to the grid electrode at greater than or equal to fifteen pulses per second. In certain embodiments, the stored instructions further adapt the controller to provide closed loop control over the power source. In certain embodiments, the grid conductor is disposed within a cable that includes one or more filament conductors each operative to provide a tube current of the electromagnetic ray tube.

Accordingly, as will be appreciated, by transferring electrical power from a power source over the HV cable as an AC current, as opposed to a DC current, some embodiments of the present invention reduce and/or eliminate capacitance between a grid conductor and any filament conductors also disposed within the HV cable, which in turn, may improve the speed at which the tube current can be cycled on and/off. For example, some embodiments of the present invention may provide for transition times for the grid voltage on the order of less than or equal to fifty microsecond (50 us). As will be appreciated, such embodiments are advantageous for vascular applications such as pulsed fluoro mode imaging which requires fast/rapid switching of the X-ray tube at low and moderate mA.

Further, some embodiments of the present invention may provide for grid voltages that can be pulsed at frame rates of about fifteen hertz (15 Hz) having a pulse width that is variable from about two milliseconds (2 ms) to a fraction of the frame rate period, e.g., twenty percent (20%) at one-hundred hertz (100 Hz) for about two milliseconds (2 ms), and/or about fifty percent (50%) at seven-point-five hertz (7.5 Hz) for about sixty milliseconds (60 ms). By providing fast/improved transitions of the grid voltage, as compared to traditional systems, some embodiments of the present invention provide for improved image quality and operational safety of ray tubes, which both tend to be dependent on sharp transitions of the grid voltage.

Further, by achieving grid voltage transition times less than or equal to fifty microseconds (50 us) without need of a mini high voltage tank disposed on the electromagnetic ray tube, some embodiments of the present invention provide for a grid-controlled electromagnetic ray based imaging system that is well suited for vascular, and/or other applications, where there is a need to keep the amount/size of imaging equipment in the vicinity of the patient at a minimum in order to maintain adequate room for surgeons and/or other medical professionals to perform certain medical procedures.

Additionally, while the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, terms such as "first," "second," "third," "upper," "lower," "bottom," "top," etc. are used merely as labels, and are not intended to impose numerical or positional requirements on their objects. Further, the limitations of the following claims are not written in means-plus-function format are not intended to be interpreted as such, unless and until such claim limitations expressly use the phrase "means for" followed by a statement of function void of further structure.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described invention, without departing from the spirit and scope of the invention herein involved, it is intended that all of the subject matter of the above description shown in the accompanying drawings shall be interpreted merely as examples illustrating the inventive concept herein and shall not be construed as limiting the invention.

What is claimed is:

1. A system for grid control of an electromagnetic ray tube, the system comprising:
   a power source disposed apart from the electromagnetic ray tube and operative to generate an AC current;
   a rectifier integrated into the electromagnetic ray tube and electrically coupled to a grid electrode of the electromagnetic ray tube;
   a grid conductor that electrically couples the power source to the rectifier; and
   wherein the rectifier is operative to convert the AC current to a DC current that powers the grid electrode.

2. The system of claim 1, wherein the grid conductor is disposed within a cable that includes one or more filament conductors each operative to provide a tube current of the electromagnetic ray tube.

3. The system of claim 2, wherein the cable is a capacitor in a resonant circuit of the power source.

4. The system of claim 2, wherein the cable has a length of between about 5 m to about 38 m.

5. The system of claim 2, wherein the cable has a RC time constant of less than or equal to 50 us.

6. The system of claim 1 further comprising:
   a transformer integrated into the electromagnetic ray tube in-between the grid conductor and the rectifier.

7. The system of claim 1, wherein the AC current has a frequency of between about 100 kHz to about 1,000 kHz.

8. The system of claim 1 further comprising:
   a controller operative to provide closed loop control of the power source.

9. A method for grid control of an electromagnetic ray tube, the method comprising:
   generating an AC current via a power source disposed apart from the electromagnetic ray tube;
   conducting the AC current to a rectifier via a grid conductor, the rectifier integrated into the electromagnetic ray tube;
   converting the AC current to a DC current via the rectifier; and
   powering a grid electrode of the electromagnetic ray tube via the DC current.

10. The method of claim 9, wherein the grid conductor is disposed within a cable that includes one or more filament conductors each operative to provide a tube current of the electromagnetic ray tube.

11. The method of claim 10, wherein the cable is a capacitor in a resonance circuit of the power source.

12. The method of claim 10, wherein the cable has a length of between about 5 m to about 38 m.

13. The method of claim 10 further comprising:
   pulsing the DC current to the grid electrode at greater than or equal to 15 pulses per second.

14. The method of claim 9 further comprising:
   transforming the AC current via a transformer integrated into the electromagnetic ray tube.

15. The method of claim 9, wherein the AC current has a frequency of between about 100 kHz to about 1,000 kHz.

16. The method of claim 9 further comprising:
   controlling the power source via a closed loop controller.

17. A non-transitory computer readable medium storing instructions that adapt a controller to:
   generate an AC current via a power source disposed apart from an electromagnetic ray tube;
   rectify the AC current to a DC current via a rectifier integrated into the electromagnetic ray tube, the rectifier electrically coupled to the power source via a grid conductor; and
   power a grid electrode of the electromagnetic ray tube via the DC current.

18. The non-transitory computer readable medium of claim 17, wherein the stored instructions further adapt the controller to:
   pulse the DC current to the grid electrode at greater than or equal to 15 pulses per second.

19. The non-transitory computer readable medium of claim 17, wherein the stored instructions further adapt the controller to:
   provide closed loop control over the power source.

20. The non-transitory computer readable medium of claim 17,
   wherein the grid conductor is disposed within a cable that includes one or more filament conductors each operative to provide a tube current of the electromagnetic ray tube.

* * * * *